(12) United States Patent
Fujisawa et al.

(10) Patent No.: US 6,509,470 B2
(45) Date of Patent: Jan. 21, 2003

(54) PROCESS FOR PREPARING TRIBROMOMETHYLSULFONYLPYRIDINE

(75) Inventors: Eiji Fujisawa, Hyogo (JP); Hiroyuki Hata, Hyogo (JP)

(73) Assignee: Sumitomo Seika Chemicals Co., Ltd., Hyogo (JP)

( * ) Notice: Subject to any disclaimer, the term of this patent is extended or adjusted under 35 U.S.C. 154(b) by 0 days.

(21) Appl. No.: 10/146,409

(22) Filed: May 14, 2002

(65) Prior Publication Data

US 2002/0128484 A1 Sep. 12, 2002

Related U.S. Application Data

(62) Division of application No. 09/959,237, filed as application No. PCT/JP00/03008 on May 10, 2000, now Pat. No. 6,420,564.

(30) Foreign Application Priority Data

May 14, 1999 (JP) ........................................... 11-134533

(51) Int. Cl.[7] ............................................ C07D 213/70
(52) U.S. Cl. ....................................................... 546/290
(58) Field of Search .......................................... 546/290

(56) References Cited

U.S. PATENT DOCUMENTS 3,702,253 A 11/1972 Winter et al.

FOREIGN PATENT DOCUMENTS

JP 11-242304 9/1999

OTHER PUBLICATIONS

Tröger, Hille, "Über arylsufonierte Amide, Nitrile und Thioamide der Essigsäure," Journal Fuer Praktische Chemie, Leipzig, DE, vol. 71, 1905, pp. 201–235.

Farrer W. V., "Trichloromethyl Sulphones and Related Compounds," Journal of the Chemical Society, Chemical Society, Letchworth, GB, 1956, pp. 508–513.

N. Furukawa, et al., "ipso–Substitution of a Sulphinyl or Sulphonyl Group Attached to Pyridine Rings and its Application for the Synthesis of Macrocycles," Journal of the Chemical Society, Perkin Transactions 1, Chimical Society Letchworth, GB, vol. 8, 1984, pp. 1839–1845.

Naomichi Furukawa, et al., ipso–Substitution of a Sulphinyl or Sulphonyl Group Attached to Pyridine Rings and its Application for the Synthesis of Macrocycles, Journal of the chemical Society, No. 8 Aug. 1984, pp. 1839–1845.

D. L. Fields, Jr et al., Homolytic Reactions of Phenyl Tribromomethyl Sulfone and Olefins, The Journal of Organic Chemistry, Aug. 22, 1986, vol. 51, No. 17 pp. 3369–3371.

*Primary Examiner*—Patricia L. Morris
(74) *Attorney, Agent, or Firm*—Knobbe, Martens, Olson & Bear LLP

(57) ABSTRACT

The present invention provides a process for preparing a tribromomethylsulfonylpyridine, which comprises reacting a methylthiopyridine and a hypobromite in the presence of a base and water in a heterogeneous system. According to the present invention, it is possible to prepare a tribromomethylsulfonylpyridine industrially advantageously, and with high yield and high purity.

6 Claims, No Drawings

PROCESS FOR PREPARING TRIBROMOMETHYLSULFONYLPYRIDINE

This application is a divisional of U.S. Patent Application No. 09/959,237, filed Oct. 17, 2001, now U.S. Pat. No. 6,420,564, which is a 371 of PCT/JP00/03008 filed May 10, 2000, which claim priority based on Japanese Patent Application No. 1999-134533, filed May 14, 1999.

TECHNICAL FIELD

The present invention relates to a novel process for preparing a tribromomethylsulfonylpyridine using a methylthiopyridine as an intermediate, and a novel process for preparing a methylthiopyridine using a halogenated pyridine as a starting material.

Tribromomethylsulfonylpyridines are useful compounds in that, if used as a constituent component of a photosensitive resin composition, a tribromomethylsulfonylpyridine will generate halogen radicals upon irradiation with active rays such as visible rays, ultraviolet rays or a laser beam, thus producing a hydrogen halide, and improving the adhesion between the photosensitive resin and a substrate.

BACKGROUND ART

An example of a process for preparing a tribromomethylsulfonylpyridine is, as shown in the undermentioned equation, to use a pyridinethiol as a starting material, produce a methylthiopyridine by thiomethylating using a methylating agent such as a methyl halide, next oxidize to produce a methylsulfonylpyridine, and then brominate to obtain the tribromomethylsulfonylpyridine.

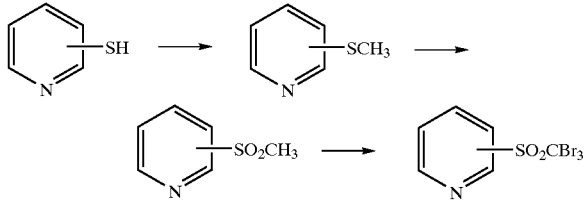

The pyridinethiol as a starting material is generally obtained by reacting a halide compound and thiourea in an alcohol, but there is a problem that the reaction yield is low. Moreover, known methods of oxidizing a methylthio compound to synthesize a methylsulfone include a method using any of various oxidizing agents such as hydrogen peroxide in the presence of an acid catalyst, and a method using any of various oxides in the presence of an acid catalyst in an acetic acid solvent. However, if a pyridine derivative is oxidized in the presence of an acid catalyst using such a method, then the nitrogen atom in the pyridine ring will also be oxidized, resulting in generation of an N-oxide as a by-product. Such N-oxides are hazardous, being prone to explosion and the like, which creates a large problem in the industrial manufacture of sulfones.

Moreover, a method disclosed in J. Org. Chem. (Vol. 51, page 3369, 1986) is known as a method of obtaining a tribromomethylsulfonylpyridine by brominating a methylsulfonylpyridine. In this method, sodium hypobromite is used as the brominating agent, the methylsulfonylpyridine is dissolved homogeneously in a mixed dioxane-water solvent, and reaction is carried out at room temperature under strongly alkaline conditions, thus obtaining the tribromomethylsulfonylpyridine; 24 hours is required for the reaction. However, in this method, the amounts used of the alkali and the sodium hypobromite are extremely large, being 21.5 mol and 6 mol respectively per mol of the methylsulfonylpyridine as a starting material. In particular, the sodium hypobromite must be used in an amount double the theoretical amount (3 mol per mol of the methylsulfonylpyridine). Moreover, the required reaction time of 24 hours is long, and the tribromomethylsulfonylpyridine obtained has poor purity, resulting in recrystallization being necessary before use. The method is thus not particularly good from an industrial point of view.

DISCLOSURE OF INVENTION

An object of the present invention is to provide a process for preparing a tribromomethylsulfonylpyridine that is industrially advantageous, allowing the tribromomethylsulfonylpyridine to be obtained easily, in a short time, and at a high yield and a high purity.

Another object of the present invention is to provide a novel process for preparing a methylthiopyridine, which is an intermediate in the preparation of a tribromomethylsulfonylpyridine.

The inventors of the present invention carried out assiduous studies to attain the above objects, and as a result discovered that by reacting a methylthiopyridine and a hypobromite in the presence of a base and water in a heterogeneous system, oxidation and bromination are carried out simultaneously, and hence a tribromomethylsulfonylpyridine can be obtained through a single stage reaction.

Moreover, the inventors of the present invention also discovered that by reacting a halogenated pyridine and an alkali metal salt of methanethiol in the presence of a base and water in a heterogeneous system, a methylthiopyridine can be obtained easily.

Furthermore, the inventors of the present invention also discovered that by continuing on to react a methylthiopyridine produced through the above reaction with a hypobromite in the presence of a base and water in a heterogeneous system, a tribromomethylsulfonylpyridine can be prepared using a halogenated pyridine as a starting material through a series of reactions in a single vessel.

The present invention thus provides processes for preparing a tribromomethylsulfonylpyridine and processes for preparing a methylthiopyridine as follows.

1. A process for preparing a tribromomethylsulfonylpyridine, which comprises reacting a methylthiopyridine and a hypobromite in the presence of a base and water in a heterogeneous system.
2. The process for preparing a tribromomethylsulfonylpyridine according to 1 above, wherein the hypobromite is sodium hypobromite.
3. The process for preparing a tribromomethylsulfonylpyridine according to 1 or 2 above, wherein the base is a hydroxide of an alkali metal.
4. A process for preparing a methylthiopyridine, which comprises reacting a halogenated pyridine and an alkali metal salt of methanethiol in the presence of a base and water in a heterogeneous system.
5. The process for preparing a methylthiopyridine according to 4 above, wherein the alkali metal salt of methanethiol is sodium methanethiolate.
6. The process for preparing a methylthiopyridine according to 4 or 5 above, wherein reaction is carried out in the presence of a phase transfer catalyst.
7. The process for preparing a methylthiopyridine according to 6 above, wherein the phase transfer catalyst is a quaternary ammonium salt or a quaternary phosphonium salt.

8. A process for preparing a tribromomethylsulfonylpyridine, which comprises reacting a halogenated pyridine and an alkali metal salt of methanethiol in the presence of a base and water in a heterogeneous system to obtain a methylthiopyridine, and then reacting the methylthiopyridine and a hypobromite in the presence of a base and water in a heterogeneous system.

9. The process for preparing a tribromomethylsulfonylpyridine according to 8 above, wherein the halogenated pyridine is 2-chloropyridine.

[Preparation of Methylthiopyridine]

A process for preparing a methylthiopyridine according to the present invention is characterized by reacting a halogenated pyridine and an alkali metal salt of methanethiol in the presence of a base and water in a heterogeneous system.

There are no particular limitations on the halogenated pyridine used in the present invention, but examples include 2-halogenated pyridines, 3-halogenated pyridines and 4-halogenated pyridines, with specific examples thereof including 2-chloropyridine, 3-chloropyridine, 4-chloropyridine, 2-bromopyridine, 3-bromopyridine and 4-bromopyridine. Out of these, 2-chloropyridine is preferably used.

There are no particular limitations on the alkali metal salt of methanethiol used in the present invention, but examples include the potassium salt of methanethiol (potassium methanethiolate) and the sodium salt of methanethiol (sodium methanethiolate). Of these, from an economic standpoint, sodium methanethiolate is preferably used. The amount used is generally in a range of 1 to 3 mol, preferably 1 to 2 mol, per mol of the halogenated pyridine. If the amount used of the alkali metal salt of methanethiol is less than 1 mol, then the amount of unreacted halogenated pyridine will become large, whereas it is economically disadvantageous to use an amount greater than 3 mol, since then effects commensurate with the amount used will not be obtained.

Examples of the base used in the present invention are alkali metal hydroxides such as sodium hydroxide and potassium hydroxide. Of these, from an economic standpoint, sodium hydroxide is preferably used. The amount used is generally in a range of 0.05 to 2 mol, preferably 0.1 to 1 mol, per mol of the halogenated pyridine. If the amount used of the base is less than 0.05 mol, then the amount of unreacted halogenated pyridine will become large, whereas it is economically disadvantageous to use an amount greater than 2 mol, since then effects commensurate with the amount used will not be obtained.

In the process for preparing a methylthiopyridine according to the present invention, the reaction between the halogenated pyridine and the alkali metal salt of methanethiol is carried out in a two-phase system since the halogenated pyridine as a starting material is not soluble in water. It is preferable to add a phase transfer catalyst to the reaction system, since then the reaction tends to proceed smoothly. A quaternary ammonium salt such as tetrabutylammonium chloride or tetrabutylammonium bromide, a quaternary phosphonium salt such as tetrabutylphosphonium chloride or tetrabutylphosphonium bromide, or the like is preferably used as the phase transfer catalyst. The amount used is generally in a range of 0.1 to 50 wt %, preferably 1 to 20 wt %, relative to the halogenated pyridine. If the amount used of the phase transfer catalyst is less than 0.1 wt %, then an adequate catalytic effect will not be obtained, whereas it is economically disadvantageous to use an amount greater than 50 wt %, since then effects commensurate with the amount used will not be obtained.

There are no particular limitations on the amount of water used in the reaction, but a suitable amount is 150 to 1000 g per mol of the halogenated pyridine.

The reaction temperature is generally in a range of 50 to 110° C., preferably 80 to 105° C. If the reaction temperature is less than 50° C., then the rate of reaction will be low, and hence a long time will be required for the reaction. If, on the other hand, the reaction temperature is greater than 110° C., then the rate of reaction will be high, but there will be increased production of by-products.

The reaction time is generally in a range of 2 to 10 hours.

The reaction is carried out in a liquid-liquid heterogeneous two-phase system, and hence the methylthiopyridine can be easily isolated after completion of the reaction merely by separating the two liquid phases using a normal procedure. The methylthiopyridine thus obtained can be used as is in the preparation of a tribromomethylsulfonylpyridine.

[Preparation of Tribromomethylsulfonylpyridine]

A process for preparing a tribromomethylsulfonylpyridine according to the present invention is characterized by reacting a methylthiopyridine and a hypobromite in the presence of a base and water in a heterogeneous system. In the present invention, the hypobromite fulfills the roles of both an oxidizing agent and a brominating agent, and hence the oxidation of the thio group and the bromination of the methyl group are carried out simultaneously in a single stage reaction, thus allowing the target tribromomethylsulfonylpyridine to be obtained in an industrially advantageous way.

Examples of the methylthiopyridine used in the present invention include 2-(methylthio)pyridine, 3-(methylthio)pyridine and 4-(methylthio)pyridine. Moreover, the methylthiopyridine used in the present invention may be obtained through any process, but can be obtained particularly advantageously through the process of the present invention described earlier.

There are no particular limitations on the hypobromite used in the present invention, with examples being alkali metal salts of hypobromous acid such as sodium hypobromite and potassium hypobromite. Of these, sodium hypobromite is preferably used.

There are no particular limitations on the concentration of the hypobromite used in the present invention, but it is industrially advantageous to use a concentration of 10 to 30 wt %. A hypobromite is generally used in an organic solvent-water system, and is thus consumed through reaction with the organic solvent, and hence must be added in great excess. However, in the present invention, an organic solvent is not used in the reaction, and hence the amount of the hypobromite used may be in a range of 1.01 to 1.5 times the theoretical amount relative to the methylthiopyridine, i.e. in a range of 5.05 to 7.5 mol per mol of the methylthiopyridine.

Examples of the base used in the present invention are alkali metal hydroxides such as sodium hydroxide and potassium hydroxide. Of these, from an economic standpoint, sodium hydroxide is preferably used. The amount used is generally in a range of 0.2 to 4 mol, preferably 0.5 to 2 mol, per mol of the methylthiopyridine. If the amount used of the base is less than 0.2 mol, then the amount of unreacted methylthiopyridine will become large, whereas it is economically disadvantageous to use an amount greater than 4 mol, since then effects commensurate with the amount used will not be obtained.

The reaction is carried out in a liquid-liquid (i.e. methylthiopyridine-water) heterogeneous two-phase system. However, as the reaction proceeds, the tribromomethylsulfonylpyridine produced is precipitated as a solid, and hence the system is a solid-liquid system by the time reaction is complete. After reaction is complete, the tribromomethylsulfonylpyridine can be obtained at high purity and high yield merely by filtering off the precipitated crystals.

There are no particular limitations on the amount of water used in the reaction. Nevertheless, because the tribromomethylsulfonylpyridine produced in the reaction is poorly soluble in water and thus precipitates out during the reaction as described above, the amount of water should be set considering the slurry concentration and the volume efficiency. A suitable amount of water is 500 to 4000 g per mol of the methylthiopyridine.

The reaction temperature is generally in a range of −5 to 50° C., preferably −5 to 30° C., more preferably 0 to 10° C. If the reaction temperature is less than −5° C., then the rate of reaction will be low, and hence a long time will be required for the reaction. If, on the other hand, the reaction temperature is greater than 50° C., then the rate of reaction will be high, but there will be increased production of by-products.

The reaction time is generally in a range of 2 to 10 hours.

In the process according to the present invention, after reaction is complete, a tribromomethylsulfonylpyridine having a purity sufficiently high for normal usage can be obtained merely by filtering off the reaction liquid and washing the crystals with water. Nevertheless, if a higher purity is required, then the purity can be raised by recrystallizing using monochlorobenzene or the like.

When preparing a tribromomethylsulfonylpyridine using a methylthiopyridine prepared through the process described above in '[Preparation of methylthiopyridinel]' as the starting material, one may either use the methylthiopyridine obtained by separating the two-phase reaction liquid after the reaction to prepare the methylthiopyridine has been completed, or one may use the two-phase reaction liquid as it is without separation.

It is thus possible to add a hypobromite to the two-phase reaction liquid after completion of the reaction to prepare the methylthiopyridine and continue on to carry out a second reaction in the presence of the base and water in the heterogeneous system, thus preparing a tribromomethylsulfonylpyridine from a halogenated pyridine as a starting material through a series of reactions in a single vessel.

Examples of the tribromomethylsulfonylpyridine obtained in the present invention include 2-(tribromomethylsulfonyl)pyridine, 3-(tribromomethylsulfonyl)pyridine and 4-(tribromomethylsulfonyl)pyridine.

According to the processes of the present invention, it is possible to prepare a tribromomethylsulfonylpyridine from a halogenated pyridine industrially advantageously, through simple and economical means, and with high yield and high purity.

Moreover, because organic solvents are not used in the present invention, the time and cost associated with recovering organic solvents are eliminated, which is industrially advantageous.

Furthermore, in the processes of the present invention, there is virtually no production of N-oxides, and hence the processes can be implemented safely, even industrially.

BEST MODE FOR CARRYING OUT THE INVENTION

Following is a more detailed description of the present invention through examples. However, it should be noted that the present invention is not limited whatsoever by these examples.

EXAMPLE 1

An aqueous solution consisting of 11.5 g (0.24 mol) of sodium methanethiolate, 6.3 g (0.15 mol) of 95% sodium hydroxide and 38.3 g of water was instilled into a mixed liquid consisting of 22.7 g (0.20 mol) of 2-chloropyridine, 2.3 g of tetrabutylammonium bromide and 2.3 g of water over 2 hours at a temperature of 80 to 90° C., and stirring was then carried out for 5 hours at 90 to 100° C. The two-phase reaction liquid thus obtained was separated, and 23.8 g of 2-(methylthio)pyridine was obtained as the upper layer. The yield relative to the 2-chloropyridine was 95.0%.

EXAMPLE 2

An aqueous solution consisting of (i) 522.7 g (1.2 mol) of a 27% sodium hypobromite aqueous solution prepared by instilling bromine into a 30% sodium hydroxide aqueous solution and (ii) 5.1 g (0.12 mol) of 95% sodium hydroxide was cooled to 0° C. The 23.8 g of 2-(methylthio)pyridine obtained in Example 1 was instilled into this aqueous solution over 2 hours while keeping the temperature at 0 to 5° C., and stirring was then carried out for 5 hours at 5 to 10° C. The reaction product, which precipitated out as crystals, was filtered, washed with water, and dried, thus obtaining 68.8 g of 2-(tribromomethylsulfonyl)pyridine (purity 99%). The yield relative to the 2-(methylthio)pyridine was 91.9%. The melting point of the 2-(tribromomethylsulfonyl)pyridine obtained was 160 to 161° C.

EXAMPLE 3

An aqueous solution consisting of 11.5 g (0.24 mol) of sodium methanethiolate, 12.6 g (0.3 mol) of 95% sodium hydroxide and 38.3 g of water was instilled into a mixed liquid consisting of 22.7 g (0.20 mol) of 2-chloropyridine, 6.8 g of tetrabutylammonium bromide and 2.3 g of water over 2 hours at a temperature of 80 to 90° C., and stirring was then carried out for 5 hours at 90 to 100° C. The two-phase reaction liquid thus obtained was separated, and 23.0 g of 2-(methylthio)pyridine was obtained as the upper layer. The yield relative to the 2-chloropyridine was 91.9%.

EXAMPLE 4

An aqueous solution consisting of (i) 522.7 g (1.2 mol) of a 27% sodium hypobromite aqueous solution prepared by instilling bromine into a 30% sodium hydroxide aqueous solution and (ii) 11.4 g (0.27 mol) of 95% sodium hydroxide was cooled to 0° C. The 23.0 g of 2-(methylthio)pyridine obtained in Example 3 was instilled into this aqueous solution over 2 hours while keeping the temperature at 0 to 5° C., and stirring was then carried out for 5 hours at 5 to 10° C. The reaction product, which precipitated out as crystals, was filtered, washed with water, and dried, thus obtaining 68.1 g of 2-(tribromomethylsulfonyl)pyridine (purity 99%). The yield relative to the 2-(methylthio)pyridine was 94.1%. The melting point of the 2-(tribromomethylsulfonyl)pyridine obtained was 160 to 161° C.

EXAMPLE 5

An aqueous solution consisting of 11. 5 g (0. 24 mol) of sodium methanethiolate, 6.3 g (0.15 mol) of 95% sodium hydroxide and 38.3 g of water was instilled into a mixed liquid consisting of 22.7 g (0.20 mol) of 2-chloropyridine, 2.3 g of tetrabutylammonium bromide and 2.3 g of water over 2 hours at a temperature of 80 to 90° C., and stirring was then carried out for 5 hours at 90 to 100° C., thus obtaining a two-phase reaction liquid containing 2-(methylthio)pyridine.

Separate to the above, an aqueous solution consisting of (i) 554.4 g (1.3 mol) of a 27% sodium hypobromite aqueous solution prepared by instilling bromine into a 30% sodium hydroxide aqueous solution and (ii) 5.2 g (0.13 mol) of 95% sodium hydroxide was prepared and cooled to 0° C. This aqueous solution was then instilled into the two-phase reaction liquid obtained above over 5 hours while keeping the temperature at 0 to 5° C., and stirring was then carried out for 3 hours at 5 to 10° C. The reaction product, which precipitated out as crystals, was filtered, washed with water, and dried, thus obtaining 67.5 g of 2-(tribromomethylsulfonyl)pyridine (purity 99%). The yield relative to the 2-chloropyridine was 85.7%. The melting point of the 2-(tribromomethylsulfonyl)pyridine obtained was 160 to 161° C.

EXAMPLE 6

A two-phase mixed liquid system consisting of 22.7 g (0.20 mol) of 2-chloropyridine, 2.3 g of tetrabutylphosphonium bromide, 11.5 g (0.24 mol) of sodium methanethiolate, 2.1 g (0.05 mol) of 95% sodium hydroxide and 35 g of water was stirred for 8 hours at 80 to 90° C. The two-phase reaction liquid thus obtained was separated, and 23.8 g of 2-(methylthio)pyridine was obtained as the upper layer. The yield relative to the2-chloropyridine was 95.0%.

EXAMPLE 7

An aqueous solution consisting of (i) 522.7 g (1.2 mol) of a 27% sodium hypobromite aqueous solution prepared by instilling bromine into a 30% sodium hydroxide aqueous solution and (ii) 8.4 g (0.2 mol) of 95% sodium hydroxide was cooled to 0° C. The 23.8 g of 2-(methylthio)pyridine obtained in Example 6 was instilled into this aqueous solution over 3 hours while keeping the temperature at 0 to 5° C., and stirring was then carried out for 7 hours at 0 to 5° C. The reaction product, which precipitated out as crystals, was filtered, washed with water, and dried, thus obtaining 71.1 g of 2-(tribromomethylsulfonyl)pyridine (purity 99%). The yield relative to the 2-(methylthio)pyridine was 95.0%. The melting point of the 2-(tribromomethylsulfonyl) pyridine obtained was 160 to 161° C.

What is claimed is:

1. A process for preparing a methylthiopyridine, which comprises reacting a halogenated pyridine and an alkali metal salt of methanethiol in the presence of a base and water in a heterogeneous system.

2. The process for preparing a methylthiopyridine according to claim 1, wherein said alkali metal salt of methanethiol is sodium methanethiolate.

3. The process for preparing a methylthiopyridine according to claim 1, wherein reaction is carried out in the presence of a phase transfer catalyst.

4. The process for preparing a methylthiopyridine according to claim 3, wherein said phase transfer catalyst is a quaternary ammonium salt or a quaternary phosphonium salt.

5. The process for preparing a methylthiopyridine according to claim 2, wherein reaction is carried out in the presence of a phase transfer catalyst.

6. The process for preparing a methylthiopyridine according to claim 5, wherein said phase transfer catalyst is a quaternary ammonium salt or a quaternary phosphonium salt.

* * * * *